(12) United States Patent
Walzman

(10) Patent No.: US 11,638,655 B2
(45) Date of Patent: May 2, 2023

(54) ORIENTABLE INTRACRANIAL OCCLUSION DEVICE AND METHOD

(71) Applicant: Daniel Ezra Walzman, Bergenfield, NJ (US)

(72) Inventor: Daniel Ezra Walzman, Bergenfield, NJ (US)

(*) Notice: Subject to any disclaimer, the term of this patent is extended or adjusted under 35 U.S.C. 154(b) by 21 days.

(21) Appl. No.: 16/888,813

(22) Filed: May 31, 2020

(65) Prior Publication Data

US 2020/0360166 A1    Nov. 19, 2020

Related U.S. Application Data

(63) Continuation-in-part of application No. 16/214,130, filed on Dec. 9, 2018, now Pat. No. 11,007,048, which is a continuation-in-part of application No. 15/732,544, filed on Nov. 22, 2017, now abandoned.

(60) Provisional application No. 62/921,574, filed on Jun. 25, 2019, provisional application No. 62/497,851, filed on Dec. 5, 2016.

(51) Int. Cl.
*A61F 2/97*      (2013.01)
*A61F 2/958*    (2013.01)
*A61F 2/82*      (2013.01)

(52) U.S. Cl.
CPC ............... *A61F 2/97* (2013.01); *A61F 2/958* (2013.01); *A61F 2002/823* (2013.01)

(58) Field of Classification Search
CPC ...... A61F 2/95; A61F 2/966; A61F 2002/823; A61F 2/97; A61F 2/958; A61F 202/823
See application file for complete search history.

(56) References Cited

U.S. PATENT DOCUMENTS

| | | |
|---|---|---|
| 5,019,090 A | 5/1991 | Pinchuck |
| 5,071,407 A | 12/1991 | Termin et al. |
| 5,221,261 A | 6/1993 | Termin et al. |
| 5,306,263 A | 4/1994 | Voda |
| 5,322,064 A | 6/1994 | Lundquist |
| 5,891,057 A | 4/1999 | Chaisson et al. |

(Continued)

FOREIGN PATENT DOCUMENTS

| | | |
|---|---|---|
| WO | WO 2005/112823 | 12/2005 |
| WO | WO2005112823 A1 | 12/2005 |

(Continued)

OTHER PUBLICATIONS

PCT/US2020/035489 International Search Report and Written Opinion (dated Sep. 8, 2020).

(Continued)

*Primary Examiner* — Christopher D. Prone

(57) ABSTRACT

A method and device to correctly orient an intracranial occlusion device, such as a stent having differential porosity, with respect to desired areas of greater or lesser blood flow (e.g., branch vessels and aneurysms, respectively), said device being particularly adapted for use in treating aneurysms in intracranial or other tortuous vasculature. An intravascular device comprising a delivery catheter having a hub and angular lumen capable of constraining a pusher wire within a packaging catheter to deploy said stent in an orientation wherein the area of least porosity abuts the aneurysm, and area of maximal porosity permits blood flow to a branch or other vessel. A method of using same.

20 Claims, 7 Drawing Sheets

(56) References Cited

U.S. PATENT DOCUMENTS

| | | | |
|---|---|---|---|
| 6,547,760 B1 | 4/2003 | Samson et al. | |
| 6,723,116 B2 | 4/2004 | Tahiri | |
| 8,465,442 B2 | 6/2013 | Freed | |
| 9,775,730 B1 | 10/2017 | Walzman | |
| 2001/0037141 A1* | 11/2001 | Yee | A61M 25/00 606/108 |
| 2001/0041874 A1 | 11/2001 | Reydel | |
| 2002/0035392 A1 | 3/2002 | Wilson | |
| 2002/0111666 A1 | 8/2002 | Hart | |
| 2002/0143383 A1 | 10/2002 | Parodi | |
| 2003/0139802 A1 | 7/2003 | Wulfman | |
| 2003/0204246 A1 | 10/2003 | Chu et al. | |
| 2003/0225365 A1 | 12/2003 | Greff et al. | |
| 2005/0049607 A1 | 3/2005 | Hart et al. | |
| 2005/0049609 A1 | 3/2005 | Gunderson | |
| 2006/0229657 A1 | 10/2006 | Wasicek et al. | |
| 2006/0271162 A1 | 11/2006 | Vito et al. | |
| 2007/0060911 A1 | 3/2007 | Webster et al. | |
| 2007/0219619 A1 | 9/2007 | Dieck et al. | |
| 2008/0015674 A1* | 1/2008 | Austin | A61F 2/95 623/1.11 |
| 2008/0172122 A1 | 7/2008 | Mayberry et al. | |
| 2008/0281394 A1 | 11/2008 | Jones | |
| 2009/0192584 A1 | 7/2009 | Gerdts | |
| 2011/0118841 A1 | 5/2011 | Reiley | |
| 2012/0316632 A1 | 12/2012 | Gao | |
| 2013/0338752 A1 | 12/2013 | Geusen et al. | |
| 2014/0025151 A1 | 1/2014 | Gao | |
| 2014/0031788 A1 | 1/2014 | Sung et al. | |
| 2014/0277397 A1 | 9/2014 | Lorenzo | |
| 2014/0288631 A1 | 9/2014 | Falotico et al. | |
| 2015/0094759 A1 | 4/2015 | Wolinsky et al. | |
| 2017/0239046 A1 | 8/2017 | Essinger et al. | |
| 2018/0236205 A1 | 8/2018 | Krautkremer | |
| 2018/0243113 A1 | 8/2018 | Walzman | |
| 2018/0289884 A1 | 10/2018 | Criado et al. | |
| 2019/0151072 A1 | 5/2019 | Walzman | |
| 2020/0253766 A1 | 8/2020 | Walzman | |

FOREIGN PATENT DOCUMENTS

| | | |
|---|---|---|
| WO | WO 2018/073830 | 4/2018 |
| WO | WO 2020/251777 | 12/2020 |
| WO | WO 2020/251788 | 12/2020 |

OTHER PUBLICATIONS

PCT/US2020/035017 International Search Report and Written Opinion (dated Oct. 6, 2020).

PCT/US2021/057506 International Search Report and Written Opinion (dated Mar. 25, 2022).

* cited by examiner

ORIENTABLE INTRACRANIAL OCCLUSION DEVICE AND METHOD

CROSS-REFERENCE(S)

This is a continuation-in-part application (CIP) claiming the benefit of the priority to utility patent application Ser. No. 15/341,820 for a Flow-Diverting Covered Stent, filed Nov. 2, 2016 (2 Nov. 2016) (now U.S. Pat. No. 9,775,730 B1, issued 3 Oct. 2017); and a CIP of application Ser. No. 16/214,130 for a Caped Stent, filed Dec. 9, 2018 (9 Dec. 2018), (now U.S. Pat. No. 11,007,048), a CIP claiming the benefit of priority to application Ser. No. 15/732,544 filed Nov. 22, 2017 (22 Nov. 2017) and provisional Ser. Nos. 62/921,574, filed Jun. 25, 2019 (25 Jun. 2019; and 62/497,851 filed Dec. 5, 2016 (5 Dec. 2016); of which the entire contents of all are hereby incorporated by reference.

FIELD OF THE INVENTION

The present disclosure relates to medical devices used to treat aneurysms and fistulas within unhealthy blood vessels, more particularly, to endovascular devices, including flow-diverting, covered, caped, fenestrated, branched, and other variable-porosity stents for use in intracranial or other tortuous vasculature.

BACKGROUND OF THE INVENTION

The prior art teaches the use of a number of devices to treat aneurysms. One such device is a differentially porous stent, having asymmetrical braiding or coils, so as to create areas of lesser or greater blood flow as may be desired. Fenestrated and branched devices have been effectively employed in the aorta and its immediate branches, and other applications having larger blood vessels with little tortuosity. Although prior art has disclosed the theoretical application of such devices intracranially and in other tortuous and distal vasculature, no device or method has been described that can reliably deploy such devices in their desired radial orientation. The constraints of intracranial or other tortuous vasculature have to date precluded the use thereof in these areas.

U.S. Pat. No. 9,775,730 B (Walzman) teaches a covered stent device capable of safe and effective delivery and deployment into tortuous vessels to effectively divert blood flow away from an aneurysm, fistula, or ruptured vessel while allowing blood to flow to healthy tissue distal to the targeted treatment area and still resulting in blood stasis and thrombus formation inside the aneurysm or fistula.

U.S. Pat. Publ. No. 2019/0151072 A1 (Walzman) teaches a caped stent providing a cover having a single attachment point and a free end that can be overlapped, thereby providing better conformity to target vessels than existing covered stents.

U.S. Pat. No. 8,398,701 B2 (Berez et al.) teaches a vascular occluding device deployable via a microcatheter. The occluding device includes an asymmetrical braid or differential lattice densities, as well as and corresponding/opposite variable densities of porosity to modify blood flow in a vessel away from a pathology such as an aneurysm while maintaining flow to surrounding tissue. Berez teaches that the flexibility of the device particularly suits it for treating aneurysms in the brain. Berez describes an embodiment including less coverage on one side at the same segment along the length of the cylinder versus the other side. For example, the area having less porosity (i.e., more coverage) should be positioned to cover an aneurysm for stagnation of flow in the aneurysm and subsequent thrombosis. The other side of the device having more porosity should be positioned on one side of a vessel or covering a branch to allow continuation of adequate flow and to prevent obstruction of flow to the branch and its distal tissue. However, Berez and others have not devised a way to consistently and reliably deploy such devices in the optimal desired radial orientation, and no such devices are available.

In the extreme, an endovascular device may provide additional porosity by including a fenestration, allowing no obstruction whatsoever of blood flow to the origin of a branch vessel. This may be combined with a full cover, in the extreme embodiment, at or near an opposing side to cut blood flow to a target aneurysm or fistula altogether.

A common blood vessel difficulty is the persistent blood flow in the aneurysm sac extrinsic to an endograft. In fact, this is the most common complication after endovascular aneurysm repair (EVAR) with stent grafts. Such endoleaks are ameliorated by a number of means. For example, Walzman's utility application Ser. Nos. 15/732,147 and 15/732,365 teach the use of hydrogel to prevent endoleaks.

The prior art also teaches endovascular coiling as a minimally invasive technique performed to prevent blood from flowing into some saccular aneurysms. This treatment results in the coil inducing embolization (clotting) of the aneurysm, which prevents blood from flowing into the aneurysm, which in turn, prevents rupture and subsequent subarachnoid hemorrhage. Endovascular coiling however may result in procedural complications include thromboembolism, cerebral embolization, aneurysm perforation, parent artery occlusion, coil migration, arterial dissection, and others. The prior art also teaches stent-assisted coiling. The stent-assisted coiling also has some of the same short comings related to stent placement and placing a stent in the parent artery requires prolonged use of anti-platelet agents to reduce the risk of thrombosis-based stenosis within the stent.

Some aneurysms and fistulas are ideally treated with covered stents, which can most directly cover the hole of the fistula or the neck of the aneurysm and reconstruct the vessel wall, immediately redirecting blood flow into the normal path of the parent vessel. However, there is no covered neuro-stent currently available in the United States. The U.S. Food and Drug Administration (FDA) has examined and tested such covered neuro-stents but none has "FDA approval," which means that the FDA has not decided the benefits over the existing treatment options outweigh the potential risks for the item's planned use. Additionally, there are currently no covered stents that are effective in severely tortuous anatomy in other parts of the body, including but not limited to splenic artery aneurysms and pulmonary arteriovenous fistulas.

A potentially significant use of covered neuro-stents is for the treatment of fistulas, particularly for Carotid cavernous fistula (CCF) which is an abnormal communication between the cavernous sinus and the carotid arterial system.

Other treatment of aneurysms includes surgical clipping of an intracranial aneurysm, which involves the application of a clip across the neck of the aneurysm. This treatment has several shortcomings including that it requires an open operation and physical manipulation of the brain. Sometimes surgical bypass is considered as well, but typically is associated with even higher rates of morbidity and mortality.

Additionally, prior art teaches the use of flow diversion devices to divert flow away from the aneurysm by placing a mesh stent or a structure similar to a stent, on the aneurysm neck along the parent artery. The use of these devices allows for thrombus formation inside the aneurysm. However, increased technical complications can develop following the deployment of flow diverters.

Additionally, because they do not completely block flow, they are generally not effective in the treatment of fistulas and ruptured vessel. Similarly, there is currently no effective vessel-sparing treatment of an iatrogenic rupture of an intracranial artery. Current treatment typically requires closing the ruptured artery with coils and/or liquid embolics to stop the bleeding, usually with significant resulting morbidity from ischemic injury to that arterial territory. Furthermore, when treating aneurysms with these devices, the aneurysm thromboses over time, a lag period, and is not immediately cured. This leaves the patient at risk of aneurysmal rupture during lag period. This can be especially problematic when treating ruptured aneurysms, which have high short-term re-rupture rates. Still further, when using current flow-diverting stents, many branch vessels are often crossed with the device, often resulting in narrowing's developing at the origins of these branches and sometimes resulting in occlusions and/or injury as well.

A need exists for an endovascular device capable of endovascular intervention for immediate cure of select intravascular aneurysm or fistula, while ameliorating the difficulties and shortcomings associated with the currently available technologies. More particularly, a need exists for a covered stent which allow said stent freedom of motion and bending without kinking around tight bends in tortuous anatomy.

Most covered stents involve producing a cylinder of a stent "skeleton" or "frame" out of semirigid materials such as metal alloys, and then attaching an impermeable "cover" to said frame. The prior art teaches such attachments are diffuse and located throughout the covering of a stent, along fixed intervals of said covering and frame, and consequently significantly limit flexibility of the device.

All currently available flow-diverting stents have relatively uniform patterns of coverage and porosity throughout. No reliable means has been developed to successfully deploy a device that has differential porosity along different circumferentially radial segments.

For neuro-endovascular procedures (and other tortuous vascular anatomies), there is no known device or method allows for precise positioning of such a differentially porous device to achieve an ideal ratio of covering and porosity where desired, and allowing flow where desired. Unlike larger vasculature (e.g., aortic), devices deployed through intracranial or other tortuous, circulatory anatomy are not susceptible to manual rotation at the hub end having an effect to rotate the intracranial end.

Thus, there is a need for a device that can be reproducibly positioned/landed in the appropriate orientation, such that area of dense coverage and corresponding low porosity (or complete impermeability in an extreme case) is deployed on the desired side, while the low density of coverage and corresponding high porosity (and/or fenestration with no coverage at all in an extreme case) is deployed on the desired side. Additionally, there is a need for branched covered and flow diverting devices in distal and tortuous vasculatures. Currently such devices are not available for use in neuro-endovascular procedures, and are similarly not available in other tortuous vascular anatomies, because devices, systems, and methods to deploy such devices consistently and accurately in the desired orientation do not exist.

Therefore, were one to deploy such a device the ultimate orientation upon positioning would be random. For example, with the case just described, the exact opposite from ideal could occur. That is, the fenestration might end up over the aneurysm, thereby increasing flow to the lesion; while the area of high-density coverage might end up over the origin of a normal branch vessel, causing a lack of flow to said branch, and subsequent ischemic injury.

Again, using the extreme example of a fenestrated version of the current invention, branched devices could also be built in vivo, by deploying a fenestrated device with the fenestration over the origin of a branch, and the deploying another device from the fenestration, and into the branch. The second device can be slightly larger in diameter proximally, at the fenestration, to ensure slight overlap, without covering the primary distal branch/vessel. Similarly, a device could be built that includes multiple branches, through multiple fenestrations, provided all fenestrations are in proper relative distance and orientation to the native branches.

This concept was described elegantly by Ruiz in U.S. Pat. No. 6,261,273 B1 for an Access System for Branched Vessels [and] Methods of Use. However, Ruiz discloses the building of a directional sheath or catheter in vivo, rather than an implant. Like the Berez device, however, the Ruiz device can work easily in straight anatomy of short distances, where a catheter can easily and accurately be rotated along its entire length from its proximal hub.

Rotation is not effective for positioning in tortuous and/or longer vascular anatomies, in which catheters do not respond in a similarly predictable fashion. This presents a difficulty when a stent device, which is usually crimped for delivery, is advanced into a delivery catheter, typically using a delivery wire and/or hypotube, in a particular arrangement. The stent will exit the delivery catheter in an unpredictable arrangement or orientation.

Furthermore, "Y" shaped flow-diverting stents were not heretofore practical to deploy or assemble at branches in cranial or other tortuous vascular anatomy. There are difficulties when these stents, with relatively lower porosity, cross a branch and adversely affect flow to said crossed branch. Additionally, such devices can typically not be crossed with an additional wire, microcatheter, and/or stent, as the pores are not sufficiently large. There exists a need for Y, bifurcated, and otherwise branched stent devices that may be effectively deployed or assembled in such anatomy. Additionally, in order to safely deploy such branches without safely and accurately, and overlapping the fenestration only slightly consistently, novel devices and methods are needed to more precisely land the proximal end of such stent devices.

Thus, a need exists for a covered or partially covered neuro stent capable of use intracranially or in other tortuous anatomy outside of the brain, which device's more porous and less porous areas may be positioned as desired with respect to one or more branch vessels and at least one aneurysm or fistula, respectively. Additionally, there is a need for similar covered or partially covered branched devices as well. The present invention satisfies these unmet needs.

SUMMARY OF THE INVENTION

The present invention discloses some embodiments that may incorporate a hypotube rather than a solid wire to cross the stenosis and act as a rail for subsequent delivery of angioplasty balloons and stents. Such a hypotube may additionally be capable of delivering fluids therethrough, thereby reducing the sump effect on the brain from flow reversal, while still maintaining sufficient retrograde flow to overcome any flow from the external carotid artery and maintain retrograde flow across the lesion during angioplasty and stenting, to minimize the risk of distal intracranial emboli.

Disclosed also is a method and device to correctly orient an intracranial occlusion device, such as a stent having differential porosity, with respect to desired areas of greater or lesser blood flow (e.g., branch vessels and aneurysms, respectively). The present invention is particularly adapted for use in treating aneurysms and fistulas in intracranial or other tortuous vasculature.

There is difficulty in achieving such a desired orientation due to several factors. The lumen of delivery catheters (through which stents may be deployed) are typically round. As such, stents will generally rotate in said lumen during deployment in an unpredictable, fashion. Additionally, as catheters are advanced through tortuous anatomy, the catheters themselves can twist, and do so in unpredictable fashion. Achieving the desired radial placement of a device, therefore, becomes a matter of chance, with a concomitant chance of achieving the opposite of the desired result, with negative consequences. The following devices and procedures are disclosed to overcome this difficulty.

Differentially porous stent or such braided-, mesh-, or weave-type therapeutic devices may be oriented to a degree of desired flow or blockage.

A stent optionally having a free-floating cover. Said floating cover is designed to optimize insertion in tortuous anatomy. Among its unique structural elements are a single circumferential attachment point at one end (as small as 1 nm), overlapping circumferential shingles and overlapping geometric shingles.

The disclosed device may optionally be deployed under flow arrest, via pharmacologic means, or via delivery through a balloon guide catheter with temporary balloon inflation or other means, to minimize the possibility of blood flow affecting positioning as it is unsheathed.

In still other embodiments, said coverings may not fully encircle a given segment of said frame, thus allowing some stents to be covered along a portion of its circumference while being uncovered at a different circumferential side of the same segment. This can sometimes allow preservation of the origin of a branch vessel that might arise from the parent vessel along the same segment of said parent vessel; for example, opposite to a fistula or the neck of an aneurysm.

The present invention further discloses devices and method to more accurately position the proximal end of a stent, so the if a fenestration in a first stent is placed over the origin of a branch, and second stent can be accurately landed to overlap the most proximal segment of the second stent only slightly with the first stent around the fenestration, so as to avoid leaks between the two stent while also avoiding unwanted obstruction of the primary vessel by said proximal end of said second stent.

More accurate "landing" of a proximal end of a stent can be achieved with the unique devices and methods described herein. We describe an inner "unsheathing" hypotube or wire, which at its distal ends has a reverse cone "wings" that can come back and cover a stent. The stent can be mounted on the distal end of an outer hypotube. The inner hypotube or wire goes through the outer hypotube, with its wings extending back over the distal end of the outer hypotube, and over the stent mounted thereon, and constrains the stent, which is typically self-expanding. Once the stent is in the desired position, the outer hypotube can be held in place, while the inner hypotube or wire is advanced. As the inner hypotube or wire is advanced, its back wings are also advanced, and releases its constraint from the stent in a proximal to distal fashion. Thereby, the proximal stent is released from its constraint first, and expands for deployment. If the proximal portion position of landing is not optimal, it can be re-sheathed by pulling the inner hypotube back again. The stent can then be repositioned and deployment can resume again.

Some embodiments may incorporate a hypotube rather than a solid wire to cross the stenosis and act as a rail for subsequent delivery of angioplasty balloons and stents. Such a hypotube may additionally be capable of delivering fluids therethrough, thereby reducing the sump effect on the brain from flow reversal, while still maintaining sufficient retrograde flow to overcome any flow from the external carotid artery and maintain retrograde flow across the lesion during angioplasty and stenting, to minimize the risk of distal intracranial emboli.

Additionally, in some embodiments, irrigation through an angioplasty balloon and/or its delivery catheter may be possible. Additionally, in some embodiments an additional balloon mounted on an angioplasty balloon catheter and/or the wire or hypotube, or a separate balloon, may serve to occlude the carotid artery distally during portions of the procedure, to prevent distal emboli while minimizing sumping of flow from the brain. Flow reversal can then be applied for a shorter duration during and after balloon deflation.

Additionally, in some embodiments a series of angioplasty balloons and/or stent(s) and their delivery catheters may be delivered sequentially over each other, over the prior, to minimize the number of device exchanges required, thereby reducing procedural times and associated risks.

The present invention also discloses the embodiments noted above in the form of branching stents.

Additional embodiments may include Y configuration stents, in which the first stent has increased porosity with larger pores over the origin of a branch vessel, and the second stent, which traverses said larger pores over the origin of the branch vessel, has increased porosity where it crosses the primary vessel in which the primary stent is placed.

DETAILED DESCRIPTION OF THE INVENTION

The embodiments of the device and variants of the device of the present invention are set forth with reference to the above drawings.

Figure 1A:
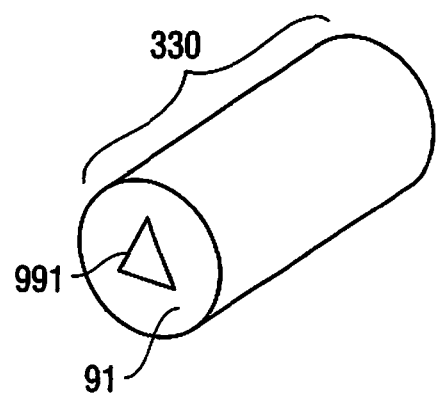
FIG. 1A shows a perspective view of a cylindrical delivery catheter 330 having a triangularly shaped lumen 991.

Referring to FIG. 1A, a perspective view is shown of a cylindrical delivery catheter 330 having a triangularly shaped lumen 991 extends from end 91. The present invention discloses a traditional cylindrical delivery catheter with a linear lumen such as a triangle, square, other rectangle, star, hexagon or so on. Said linear lumen is designed to allow the second of a push wire which has a similar shape, adapted to be inserted into said lumen 991 at differing, fixed relative positions.

Figure 1B:
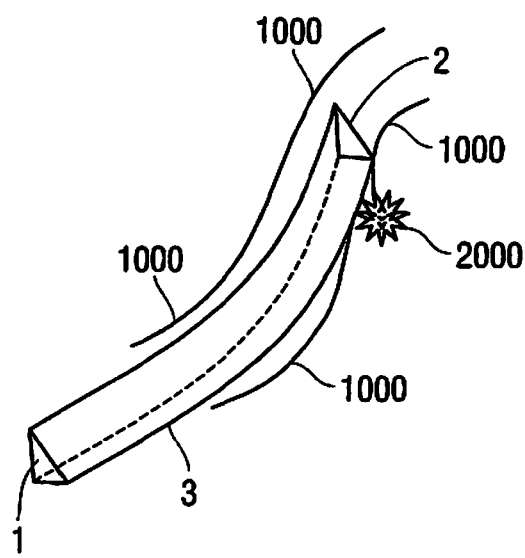
FIG. 1B shows an embodiment of delivery catheter lumen 3 without its cylindrical sheathing (not shown), having a proximal end 1 and a distal end 2, and has been passed through vessel 1000 such that distal end hole 2 in proximal to target aneurysm 2000.

Now referring to FIG. 1B, shown is an embodiment of delivery catheter lumen 3 without its cylindrical sheathing (not shown). Said delivery catheter lumen 3 having a proximal end 1 and a distal end 2, and has been passed through vessel 1000 such that distal end hole 2 in proximal to target aneurysm 2000. Delivery catheter lumen 3 is inserted into blood vessel 1000 until stopped such that distal end 2 is proximal to target aneurysm 2000. Due to the linear geometry of the lumen 1, the delivery catheter lumen 3 has a set orientation with respect to having one side closest to said target aneurysm 2000.

Figure 1C:
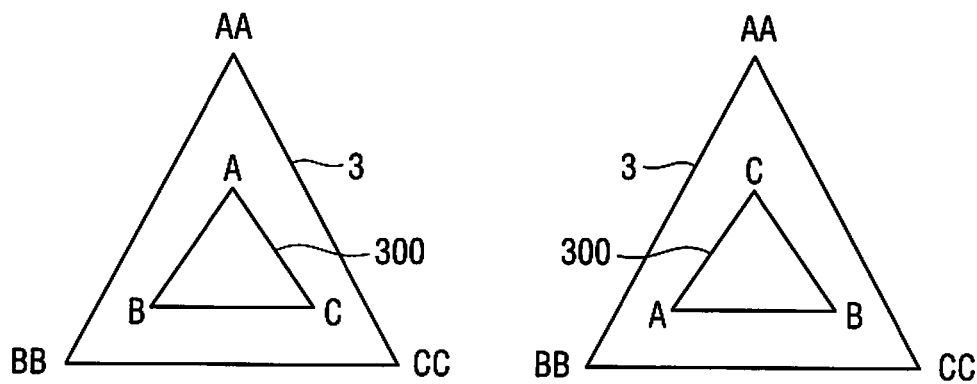
FIG. 1C is a cutaway view of delivery catheter lumen 3 having a triangular lumen with ABC angles, and pusher wire 300 passing therethrough at offset C-A-B angles, in order to deliver a differentially porous occlusion device (not shown) at a 120° angle to deploy at a desired orientation.

Now referring to FIG. 1C, shown is a cutaway view of delivery catheter lumen 3 having a triangular lumen with A-B-C angles, and pusher wire 300 passing therethrough at offset C-A-B angles, in order to deliver a differentially porous occlusion device (not shown) at a 120° angle to deploy at a desired orientation. The present invention teaches that the orientation of a push-wire may be fixed outside the patient's body by fixing its relative orientation with respect to the delivery catheter lumen 3. Said delivery catheter lumen 3's orientation with respect to target aneurysm 2000, having been established prior to insertion of push-wire 300, allows the user of the device of the present invention to properly insert said push-wire 300 to achieve proper orientation with respect to aneurysm 2000 without turning said push-wire 300 inside the patient. The present disclosure includes the basic concept of having a non-circular, geometrically shaped inner lumen and matched pusher wire or hypotube. This allows the user to avoid unwanted turns of devices inside the delivery catheter and inside of vessels. It also allows delivery in a predictable radial orientation, utilizing a marker at the hub and a corresponding radial marker at the delivery catheter tip, so that when the orientation of the delivery catheter tip is imaged after positioning intracranial, or in similar tortuous anatomy, the degree of torsion, if any, relative to the corresponding hub marker and relative to the target pathology can be measured. The stent device can then be inserted at an appropriate orientation relative to the hub marker, so that the desired orientation is delivered to the target vessel. For example, if the hub marker is at 12 o'clock, and the tip marker is at 4 o'clock, the device/stent can be inserted knowing that whatever porosity is inserted at the hub at 12 o'clock, will consistently be delivered through the catheter tip at 4 o'clock. Similarly, stent devices can be preloaded in packaging catheters of a similar geometric shape, and with a similar 12 o'clock marker (or similar), at various radial circumferential orientations relative to the 12 o'clock position. Then, depending on which orientation is desired, the appropriate preloaded device can be chosen and utilized. Alternatively, the devices can all be preloaded in the same orientation, and the packaging catheter can be rotated at various angles relative to the delivery catheter and its hub, in order to achieve the desired orientation of the stent device as it is transferred from the packaging catheter to the delivery catheter. As is well known in the prior art, the packaging catheter it typically shorter than the delivery wire or delivery hypotube. The stent is preloaded onto said delivery wire or hypotube within said packaging catheter. Transfer of said stent device is then achieved by mating the packaging catheter with the delivery catheter, within the hub of the delivery catheter, and then advancing/pushing the back of the wire/hypotube, which is extending out the back of the packaging catheter. Said wire/hypotube is advanced, together with the stent mounted thereon, at a minimum until the stent is completely within the delivery catheter, and most often until the majority of the pusher wire/hypotube is as well. The packaging catheter is the removed from the remainder of the hypotube/wire, and the operator continues to push said hypotube/wire until the stent reaches the end of the delivery catheter. The stent can then be deployed by pushing it out, retracting the delivery catheter to unsheathe it, and/or a combination of these. Additionally, in the preferred embodiments the pusher wire/hypotube, packaging catheter, and delivery catheter have a matching geometrical shape, with the packaging catheter and delivery catheters (excluding the hub) having similar inner dimensions; the wire/hypotube fits snugly, but slideably, into the packaging catheter and delivery catheter, fitting in a lock-in-key fashion, so it can advance within said catheters but cannot rotate in said catheters. For example, in one embodiment the pusher wire/hypotube has and outer triangular cross-sectional shape, which fits into an inner triangular shaped packaging catheter and delivery catheter.

Figure 2:
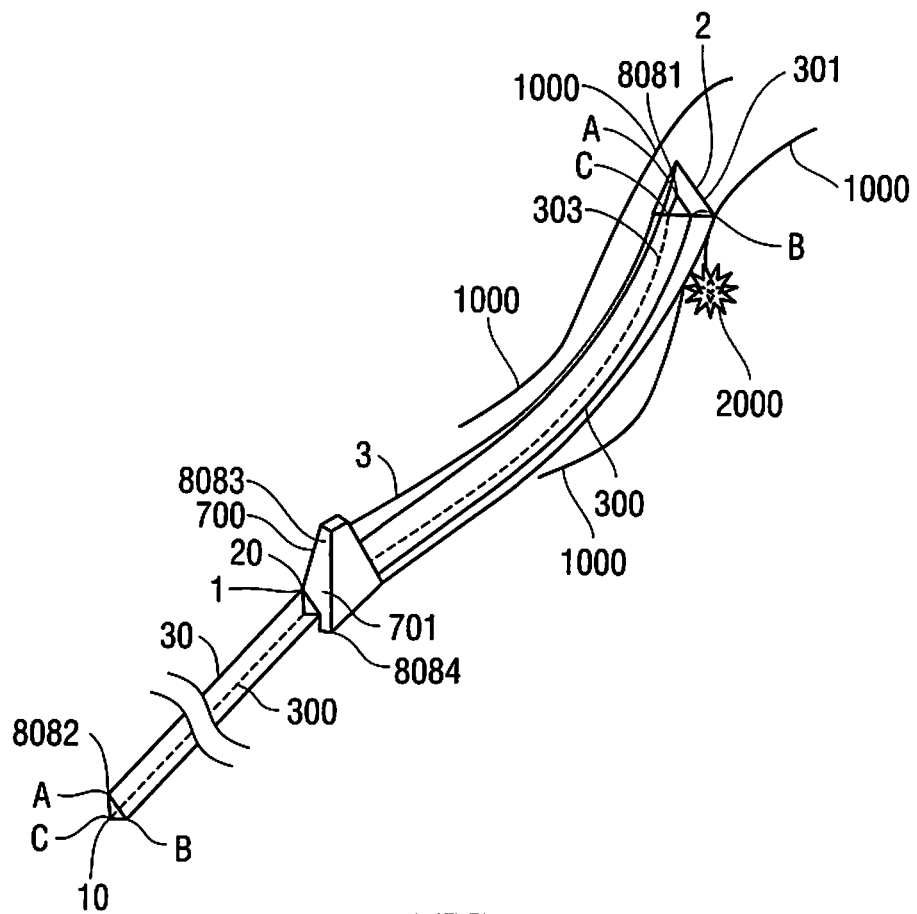
FIG. 2 shows proximal end 10 and distal end 20 of stent-packaging catheter 30 (outside patient's body), hub 700 attached to delivery catheter lumen 3, packaging-catheter hub port 701 displaying push-wire 300 running therethrough, further showing push-wire 300 (in dashed lines extending through delivery catheter lumen 3) continuing through delivery catheter lumen 3, said push-wire 300 having its distal end 303 releasably attached to stent 301 proximal to target aneurysm 2000. The distal end 20 of stent-packaging catheter 30 disposed inside hub port 701 delivery catheter lumen 3 (oriented with triangular proximal end hole 1, and triangular distal end hole 2 proximal to target aneurysm 2000); delivery catheter lumen 3 being deployed within vessel walls 1000.

Now referring to FIG. 2, shown is proximal end 10 and distal end 20 of stent-packaging catheter 30 (outside patient's body), hub 700 attached to delivery catheter lumen 3, packaging-catheter hub port 701 displaying push-wire 300 running therethrough, further showing push-wire 300 (in dashed lines extending through delivery catheter lumen 3 and continuing through delivery catheter lumen 3, said push-wire 300 having its distal end 303 releasably attached to stent 301 proximal to target aneurysm 2000; the distal end 20 of stent-packaging catheter 30 disposed inside hub port 701, delivery catheter lumen 3 (oriented with triangular proximal end hole 1, and triangular distal end hole 2 proximal to target aneurysm 2000); delivery catheter lumen 3 being deployed within vessel walls 1000.

Packaging catheter 30 is joined to hub 700 at port 701 such that stent 301 and push-wire 300 are oriented as desired so as to present the minimally porous surface of said stent 301 substantially toward the target aneurysm 2000.

Figure 3:
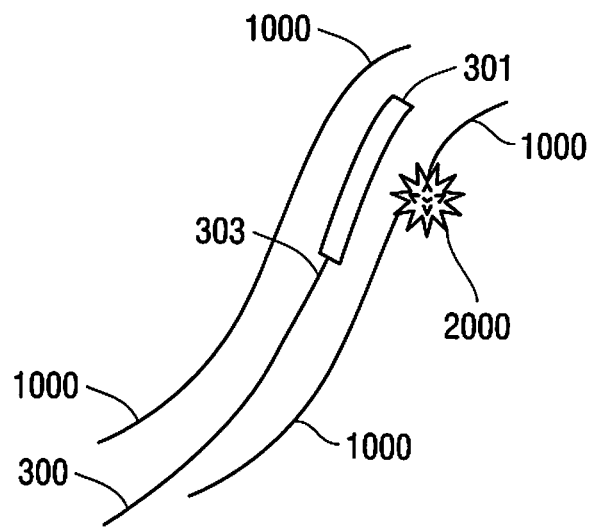
FIG. 3 shows push-wire 300 and stent 301 disposed at push-wire distal end 303 within vessel walls 1000 following removal of delivery catheter lumen 3 (shown in FIG. 2).

Now referring to FIG. 3, shown is push-wire 300 and stent 301 disposed at push-wire distal end 303 within vessel walls 1000 following removal of delivery catheter lumen 3 (shown in FIG. 2). Once stent 301 is proximally paced next to aneurysm 2000, said stent 301 is activated and expands such that the substantially nonporous side of said stent 301 abuts said aneurysm 2000, while the other two sides of a triangularly elongated stent 301 are porous to promote blood flow. Additionally, the present invention discloses a single "12 o'clock" marker on the hub, and a single radio-opaque "12 o'clock" marker on the distal catheter tip.

Figure 4:
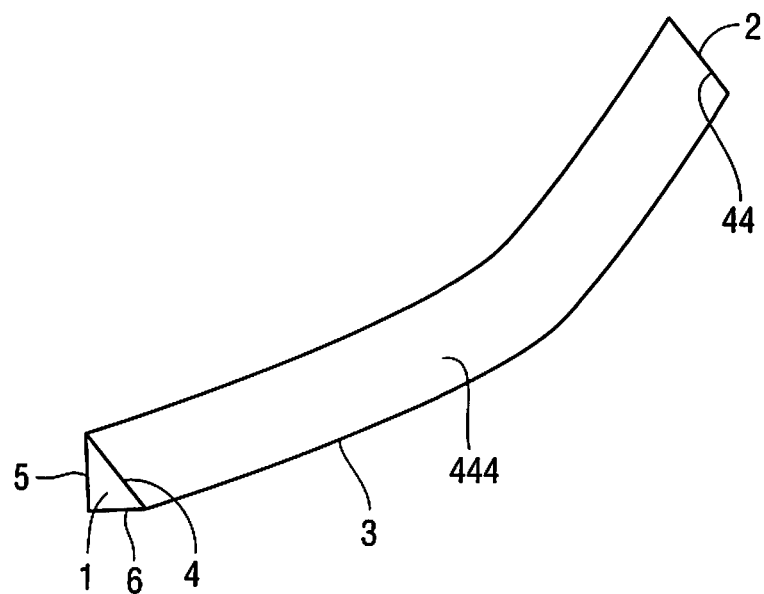
FIG. 4 shows an interior view of delivery catheter lumen 3 having a triangular shape, composed of proximal sides 4, 5 and 6, corresponding with distal sides 44 (oblique distal sides 55 and 66 behind 44 are shown in FIG. 5); facing side 444 illustrates the full length of the catheter side beginning at proximal side 4 and ending in distal side 44. Alternative embodiments (not shown) may employ other regular shapes such as rectangles or stars.
Figure 5:
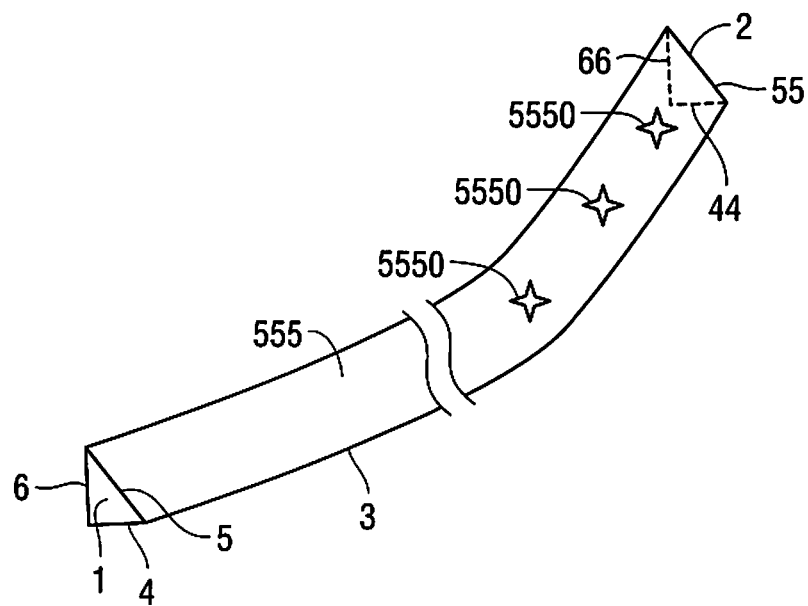
FIG. 5 shows an adjacent face 555 of the interior of delivery catheter of FIG. 4 (or FIG. 4 rotated once 120.), face 555 beginning at proximal side 5 and ending in distal side 55 (oblique distal sides 44 and 66 behind 55 shown in dashed cutaway); facing side 555 further includes radio-opaque orientation-aid markers 5550.

Now referring to FIG. 4, shown is an interior view of delivery catheter lumen 3 having a triangular shape, composed of proximal sides 4, 5 and 6, corresponding with distal sides 44 (oblique distal sides 55 and 66 behind 44 are shown in FIG. 5); facing side 444 illustrates the full length of the catheter side beginning at proximal side 4 and ending in distal side 44.

The orientation of lumen of delivery catheter lumen 3 must be clearly identifiable. FIG. 4 shows a triangular shape having sides 4, 5 and 6 on the proximal end, 44 at the distal end of face 444. Alternative embodiments (not shown) may employ other regular shapes such as rectangles or stars.

Now referring to FIG. 5, shown is an adjacent face 555 of the interior of delivery catheter of FIG. 4 (or FIG. 4 rotated once 120.), face 555 beginning at proximal side 5 and ending in distal side 55 (oblique distal sides 44 and 66 behind 55 shown in dashed cutaway); facing side 555 further includes radio-opaque orientation-aid markers 5550. FIG. 5 is a rotated image of FIG. 4 displaying the opposing plane 555 which terminates at side end 5 on the proximal end, and 55 on the distal end. On said 555 surface, radio markers 5550 allow the user to ascertain the relative orientation of one side of the delivery catheter lumen 3. Using this information, the packaging catheter 30 may be properly oriented in hub port 701 such that when push-wire 300 and stent 301 are proximal to aneurysm 2000, they are properly aligned or oriented.

Figure 6:
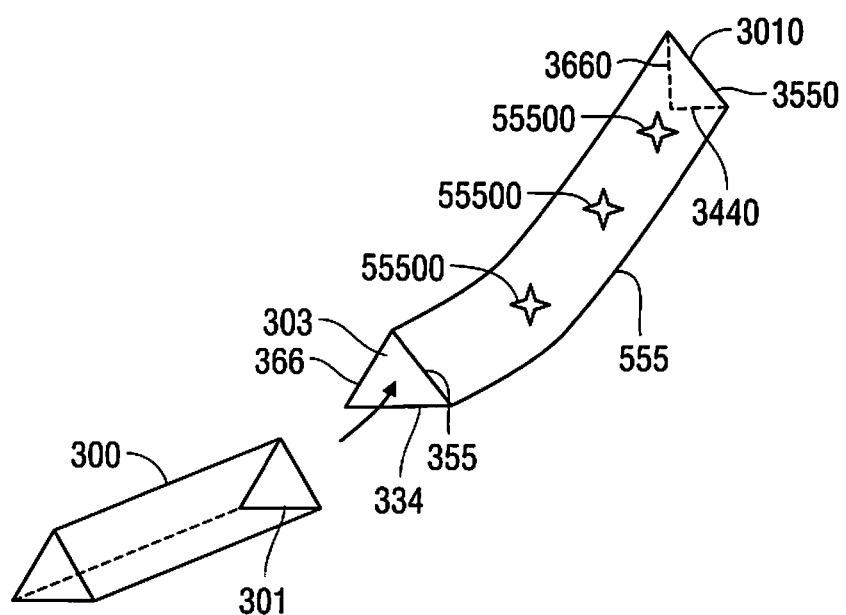
FIG. 6 shows a stent 301 attached to push-wire 300 at distal end 303 of push-wire 300 and proximal end of stent 301. Said stent 301 is triangular in shape, with distal end 3010 and triangular edges on a plane with distal end 303, namely edges 334, 355 and 366. At the distal end 3010 of stent 301, triangular edge 3550 is shown in dotted lines disclose the other two triangular edges 3440 and 3660. Triangular edge 335 forms a planar length terminating in edge 3550. On said plane, resides radio-opaque markers 55500.
Figure 7A:
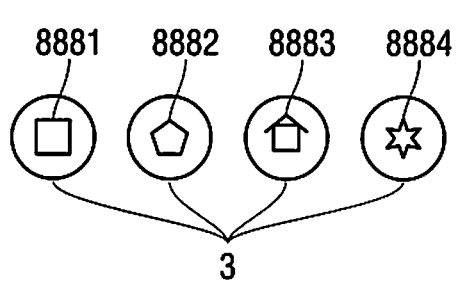
FIG. 7A and FIG. 7B show delivery catheter lumen 3 geometry with relative position of radio-opaque markers.
Figure 7B:
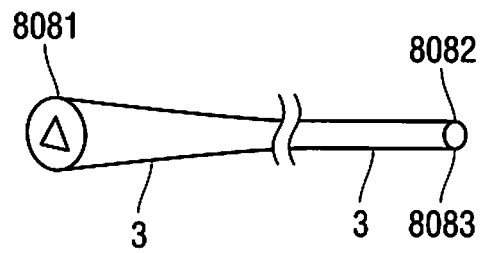
Figure 8:
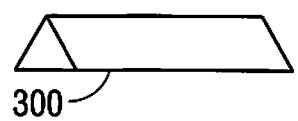
FIG. 8 shows one geometry of a pusher wire.
Figure 9:
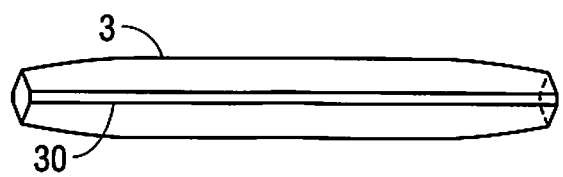
FIG. 9 shows packing catheter.
Figure 10:
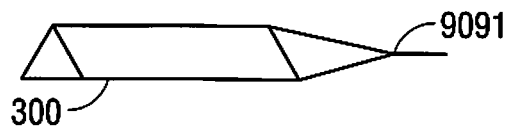
FIG. 10 shows options for packing catheter.
Figure 11:
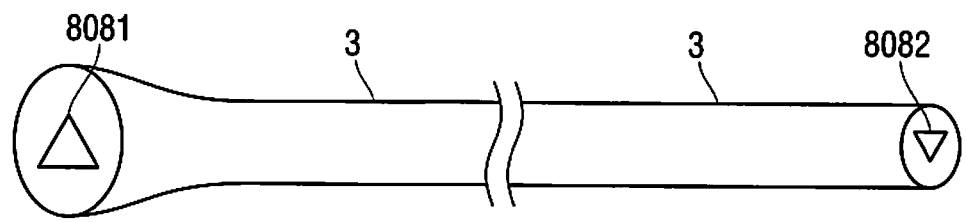
FIG. 11 and FIG. 12 shows positions of radio-opaque markers relative to each other.
Figure 12:
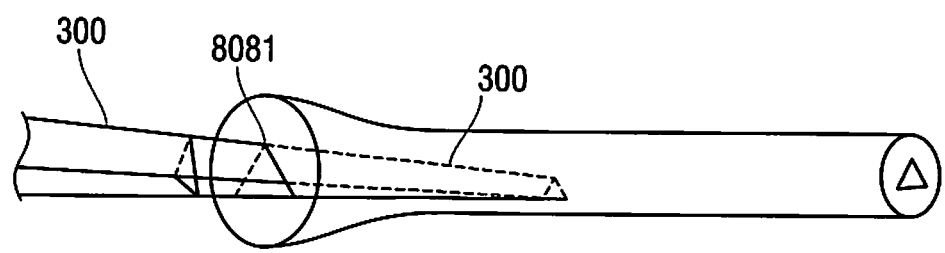
Figure 13:
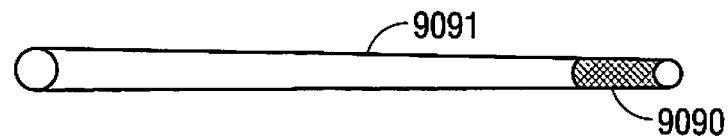
FIG. 13 and FIG. 14 show optional embodiments of reverse unsheathing stents.
Figure 14:
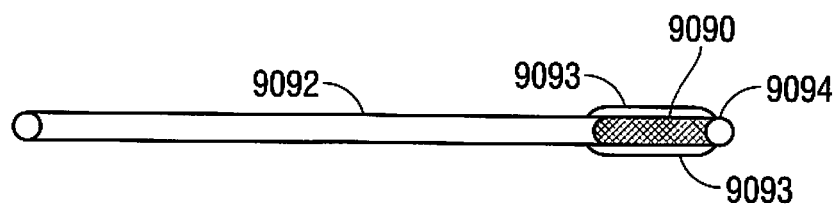
Figure 15:
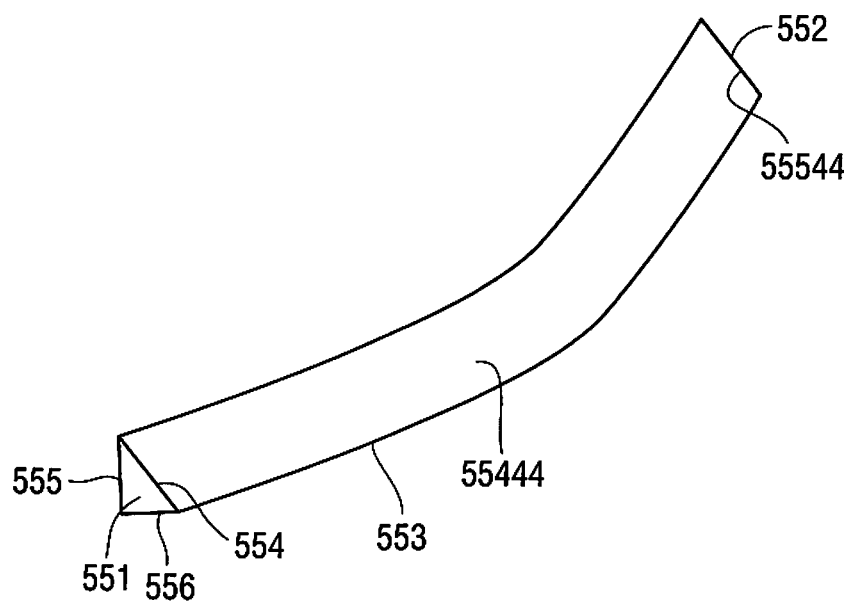

Now referring to FIG. 6, shown is a stent 301 attached to push-wire 300 at distal end 303 of push-wire 300 and proximal end of stent 301. Said stent 301 is triangular in shape, with distal end 3010 and triangular edges on a plane with distal end 303, namely edges 334, 355 and 366. At the distal end 3010 of stent 301, triangular edge 3550 is shown in dotted lines disclose the other two triangular edges 3440 and 3660. Triangular edge 335 forms a planar length terminating in edge 3550. On said plane, resides radio-opaque markers 55500.

First Method.

Use a delivery catheter with a "12 o'clock" marker at the proximal hub of said catheter. The 12 o'clock marker may be disposed on the hub and on the delivery catheter tip (i.e., radio-opaque on the catheter tip). The user inserts the stent-packaging catheter having a differentially porous stent or occlusion device mounted on a push-wire therein. After testing, the user rotates the packaging catheter at the hub to the desired indicator.

The indicator may be disposed in any position on the hub to point to any direction on the hub, but terming this a 12 o'clock indicator or marker is convenient for describing positions relative to the marker for anyone familiar with an analog clock face. For example, instructing a user to rotate the hub to "3 o'clock", "6 o'clock", or "9 o'clock" intuitively suggests a quarter turn, half turn, and three-quarter turn, respectively, with other "times" referring to approximate positions between these 90° references (e.g., 2 o'clock, 5 o'clock or 11 o'clock). The same effect could be achieved by reference to a "North" marker, utilizing terminology such as East, South, and West (or interstitial positions such as ESE or NW), but "12 o'clock" is a preferred reference. The ability to rotate the relative orientation of the delivery catheter within a 360° range manually, not the terminology employed, is material.

Use a packaging catheter having a distal marker, advance a test stent or final stent at a particular orientation relative to the 12 o'clock marker on said delivery catheter. The stent (or other marked endovascular device) will generally end in a substantially similar, but unpredictable, orientation. The process may be repeated to verify that the markers on the delivery catheter and the packaging catheter are consistently aligned. Then image the markers on the test stent/device relative to the marker on the tip of the delivery catheter to determine what orientation (i.e., at what "hour" on the "clock") the stent needs to be loaded into the delivery catheter in order to achieve the desired orientation. Or use a stent preloaded in a delivery catheter in a desired orientation relative to the "12 o'clock" marker.

Optionally, the orientation can be confirmed with an additional test stent/device which is temporarily advanced in the predicted orientation, and then imaging can confirm, before the test device is removed and a permanent device is advanced and deployed.

By way of example, a test result shows a fenestration deploys at "7 o'clock", which is 90° clockwise relative to the target branch vessel. The treatment would then reorient the stent-packaging catheter at "4 o'clock", to have it appear correctly oriented proximal to the target branch.

When a catheter tip orientation is imaged, the stent loaded in the appropriate orientation relative to the similarly disposed hub marker can be deployed. Once again, if desired, "test" device/stents with additional radio-opaque markers can be retrievably deployed to confirm the orientation.

Second Method

Disclosed is a second method, using the steps and markers of the above-described First Method, and in addition using a delivery catheter having throughout its cross section a unique geometrically shaped inner lumen. In a typical embodiment, the surface of the delivery catheter will be conventionally cylindrical, substantially rounded, to facilitate advancement through circulatory vessels. An unrounded lumen minimizes the rotational tendency of a deploying stent-packaging catheter, or a wire, enhancing the predictability of orientation.

The accompanying figures show, by way of example, a triangularly shaped lumen. Alternatively, a square, hexagon, octagon, pentagon, a "house" silhouette or star shape. Any style of star may be used, such as 6-pointed, "Star of David" or others, or other geometric shapes, provided a single one is used throughout the lumen.

In a further embodiment, a packaging catheter may be shaped correspondingly to the shape of the lumen of the delivery catheter. This correspondence is shown in the accompanying FIGS. 1A and 1B, for example. This embodiment is configured such that the correspondingly shaped packaging catheter and delivery wire/hypotube are snug enough so as to not allow rotation, but loose enough to allow movement back and forth relative to one another. This embodiment will maintain a similar orientation through the advancement of the stent/device through the delivery catheter, allowing accurate and predicable deployment in appropriate and desired orientation.

Again here, a "12 O'clock" marker that is at the same orientation can be on the hub and on the catheter tip (radio-opaque on the catheter tip). So, when/if the catheter tip orientation is imaged, the stent loaded in the appropriate orientation relative to the similarly disposed hub marker can be used. Once again, if desired, "test" device/stents with additional radio-opaque markers can be retrievably deployed to confirm the orientation. When the tip marker orientation can be well imaged after delivery intracranially, or into similar tortuous vasculature, the tip marker orientation, and its relative deflection on a rotary basis from the hub marker, can most often be used to determine rotational orientation, without the need for optional retrievable test-stent devices.

Common Method

Using any of the devices and methods above, a fenestration can be accurately deployed at the origin of a branch vessel. Then a wire can be advanced through that fenestration and into the branch, and either: (a) a balloon expandable device/stent can be delivered over the wire and deployed so that the proximal end minimally overlaps with the fenestration of the first stent/device; moreover, the branch may also optionally have a taper so it is somewhat larger at the fenestration side versus the portion that extends into the branch vessel; (b) a second delivery catheter (or the first can be re-used) can be delivered into the branch (the wire can optionally be removed) and an additional branch stent, most often self-expanding, can be delivered through the delivery catheter. Again, the branch stent may also optionally have a taper so it is somewhat larger at the fenestration side versus the portion that extends into the branch vessel.

Delivery method (b), however, has difficulty accurately landing the proximal stent, especially with "woven" or "braided" stents which can significantly, and unpredictably, foreshorten during deployment (compared to their length crimped in the delivery catheter).

Another option therefore is a novel delivery device for such stents. In this embodiment, it can be loaded in a device/catheter similar to the "inner catheter with wings" of a filter-tip TAVR (transcatheter aortic valve replacement) catheter, or said another way a "central tube" and "retaining structure connected to the distal end of said central tube and extending in a direction from the distal end to the proximal end of said central tube" also described and patented by Walzman (US1030724262). The "wings" provide the proper fixing of the orientation while being guided through the angular lumen 1 of the delivery catheter. Having a single or multiple external wires attached to a stent, in a preferred embodiment ideally attached to the proximal and distal ends of the stent (which can be "over the wire" or most ideally "rapid exchange") once a first stent is deployed with the fenestration overlying a branch vessel origin, a second wire is advanced through the fenestration into the branch, and a second stent/device, delivered constrained within said retaining structure and having at least one second wire attached to said stent outside the central tube and/or an outer tube attached to said stent, is advanced over the wire to the desired position. The stent attached wire(s) (or, alternatively, the outer catheter) is held in place while the "inner catheter with wings" is advanced, exposing/unsheathing the stent from the proximal end first.

The present invention also discloses an unsheathing device for the branch stent. More specifically the present invention teaches a device which un-sheaths the proximal part first. In the foregoing, if the stent is attached by wires, the wires can expand with the stent. If the stent is attached to an outer catheter (which is outside the inner catheter, but still inside the stent; the wings are outside the stent), it would need to wait until entire stent is unsheathed before detaching the proximal end. Or if stent is attached circumferentially proximally to an outer catheter and also has at least one additional wire attached to the stents distal segment- or additional attachment(s) to the outer catheter at the distal stent segment, then the proximal attachments can be detached upon unsheathing the proximal segment of the stent- to ensure appropriate orientation and position overlapping minimally the fenestration but not significantly overlapping/covering the primary vessel, and then the distal stent can be detached once the entire stent is deployed.

The stent can optimally be attached only distally to the "outer catheter", in order to advance the system, the outer catheter is pushed, which pulls the attached stent and pushes the winged portion of the inner catheter (and subsequently the entire inner catheter in unison). Then, when the stent is properly positioned, the second stent can be unsheathed by holding the outer catheter (with attached stent) in position and then advancing the inner catheter, which will unsheath the proximal stent first. Using self-expanding stents, the proximal stent will automatically expand as it is unsheathed. If position is off, the inner catheter can be pulled back again and the proximal stent can be re-sheathed, and the stent can be repositioned before unsheathing again.

Additionally, when using "braided" or "woven" stents, full expansion can be slow and unpredictable, the proximal end of stent (and optionally other parts as well) can have a nitinol wire ring to encourage more immediate opening/self-expansion to its maximal diameter. There may optionally be similar attached longitudinal wires as well to help allow smooth re-sheathing when desired. Such rings may optionally be repeated at additional intervals along the stent device.

More particularly, a preferred method may be described by the following steps, using the embodiment of the device in which the pusher wire comprises an angular shape congruent with the angular lumen of the delivery catheter (e.g., a triangularly shaped pusher wire and triangular lumen):

(a) inserting said delivery catheter into a body,
(b) pushing said proximal end of said delivery catheter over a delivery wire until said distal end of said delivery catheter is proximal to a target aneurysm,
(c) removing said delivery wire
(d) imaging the orientation of said distal end radial marker relative to said target aneurysm (e) orienting said packaging catheter relative to a 12 o'clock hub marker so as to optimize orientation of said stent relative to said target aneurysm, inserting said packaging catheter into said hub, (g) pushing said pusher wire until said stent is fully within said delivery catheter (h) removing said packaging catheter pushing said pusher wire until said stent is proximal to said target aneurysm, deploying the majority of said differentially porous occlusion device, (k) repeating imaging to confirm expected device orientation (l) deploying fully the remainder of said differentially porous occlusion device, and (m) withdrawing said pusher wire and said delivery catheter.

Bifurcated or V-Shaped Stents

Using the foregoing procedure, a "Y" shaped stent may be assembled from two stents in vivo by reference to markers.

The present invention may employ self-expanding components.

The present invention may employ balloon-expanding components.

The present invention may optionally contain radiopaque components and/or radiopaque markers. These can be especially valuable at ends of stent and at the ends and edges of covered zone. Radio-opaque materials and markers can also be optionally present in more places, and sometimes throughout.

The present invention may have branched stent elements.

The present invention's stent elements may optionally be fully re-sheathable.

The present invention's stent elements may optionally be partly re-sheathable.

All stent elements of the present invention may be optionally be detachable.

It will be understood by those skilled in the art that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. An intravascular system configured for insertion into a blood vessel, the intravascular device comprising:
   a delivery catheter having a longitudinal axis and having a circular cross-section perpendicular to the longitudinal axis and extending along a length of the longitudinal axis and defining an inner lumen within the circular cross section having a first non-circular configuration;
   a pusher configured for insertion into the inner lumen of the delivery catheter, the pusher having a second non-circular configuration corresponding to the first non-circular configuration so as to snugly fit to inhibit rotation of the pusher within the delivery catheter to thereby maintain a pre-determined angular orientation of the pusher within the delivery catheter; and
   a stent secured to the pusher such that the stent is deployable within the blood vessel via axial movement of the pusher through the delivery catheter.

2. The intravascular system of claim 1, wherein the first non-circular configuration of the lumen of the delivery catheter and the second non-circular configuration of the pusher are each defined by a plurality of linear segments.

3. The intravascular system of claim 2, wherein the delivery catheter includes markers to identify an angular orientation of the delivery catheter within the blood vessel.

4. The intravascular system of claim 3, wherein the markers extend along a single linear segment of the delivery catheter.

5. The intravascular system of claim 1, wherein the first non-circular configuration of the inner lumen of the delivery catheter and the second non-circular configuration of the pusher are such that the pusher is insertable into the inner lumen in at least three distinct angular orientations.

6. The intravascular system of claim 5, wherein the first non-circular configuration and the second non-circular configuration are each triangular.

7. The intravascular device of claim 5, wherein the first non-circular configuration and the second non-circular configuration are each square-shaped.

8. The intravascular device of claim 5, wherein the first non-circular configuration and the second non-circular configuration are each rectagonal.

9. The intravascular device of claim 5, wherein the first non-circular configuration and the second non-circular configuration are each hexagonal.

10. The intravascular device of claim 5, wherein the first non-circular configuration and the second non-circular configuration are each star-shaped.

11. An intravascular system configured for insertion into a blood vessel, the intravascular device comprising:
    a delivery catheter having a longitudinal axis and a circular cross section perpendicular to the longitudinal axis and extending along a length of the longitudinal axis defining an inner lumen within the circular cross-section;
    a pusher configured for axial movement through the inner lumen of the delivery catheter; and
    a stent secured to the pusher such that the stent is deployable within the blood vessel via axial movement of the pusher through the delivery catheter, the inner lumen of the delivery catheter and the pusher including corresponding non-circular cross-sectional configurations such that the pusher is within the inner lumen upon insertion into the delivery catheter to thereby maintain a pre-determined angular orientation of the stent as rotation of the pusher is limited by the corresponding non-circular cross-sectional configurations.

12. The intravascular system of claim 11, wherein the corresponding cross-sectional configurations of the inner lumen and the pusher facilitate insertion of the pusher into the inner lumen in a plurality of discrete orientations separated by a defined angular increment.

13. The intravascular system of claim 12, wherein the inner lumen and the pusher are configured such that the defined angular increment is at least 60°.

14. The intravascular device of claim 13, wherein the inner lumen and the pusher are configured such that the defined angular increment is at least 90°.

15. The intravascular device of claim 14, wherein the inner lumen and the pusher are configured such that the defined angular increment is 120°.

16. The intravascular system of claim 11, further comprising a packaging catheter having a lumen having a non-circular cross section.

17. The intravascular system of claim 11, wherein the corresponding cross-sectional configurations of the inner lumen and the pusher are selected from the group consisting of triangular, square, rectangular, hexagonal, and star-shaped.

18. An intravascular system configured for insertion into a blood vessel, the intravascular device comprising:
- a delivery catheter having a longitudinal axis and a first cross-sectional configuration perpendicular to the longitudinal axis and extending along a length defining an inner lumen within the first cross-sectional configuration and having a second cross-sectional configuration differently shaped than the first cross-sectional configuration;
- a pusher configured for insertion into the inner lumen of the delivery catheter; and
- a stent secured to the pusher such that the stent is deployable within the blood vessel via movement of the pusher through the delivery catheter, wherein the delivery catheter and the pusher are configured such that the pusher is slidable through the inner lumen in at least three discrete orientations separated by a defined angular increment.

19. The intravascular system of claim 18, wherein the inner lumen and the pusher are configured such that the defined angular increment is at least 60°.

20. The intravascular system of claim 18, wherein the inner lumen and the pusher include corresponding non-circular cross-sectional configurations.

* * * * *